United States Patent [19]

Manning

[11] Patent Number: 5,716,318

[45] Date of Patent: Feb. 10, 1998

[54] METHOD OF TREATING CARDIAC ARREST AND APPARATUS FOR SAME

[75] Inventor: James E. Manning, Chapel Hill, N.C.

[73] Assignee: The University of North Carolina at Chapel Hill, Chapel Hill, N.C.

[21] Appl. No.: 422,338

[22] Filed: Apr. 14, 1995

[51] Int. Cl.$^6$ ............................................. A61N 1/362
[52] U.S. Cl. ............................... 600/16; 128/897; 604/4
[58] Field of Search ................. 600/16–18; 128/897–98; 606/194; 604/23, 28, 49, 51, 56, 96, 97

[56] References Cited

U.S. PATENT DOCUMENTS

| | | | |
|---|---|---|---|
| 3,962,439 | 6/1976 | Yokoyama et al. | 424/248 |
| 4,686,085 | 8/1987 | Osterholm | 422/45 |
| 4,804,358 | 2/1989 | Karcher et al. | 600/17 |
| 5,024,668 | 6/1991 | Peters et al. | 606/194 |
| 5,057,120 | 10/1991 | Farcot | 606/194 |
| 5,085,630 | 2/1992 | Osterholm et al. | 604/28 |
| 5,195,942 | 3/1993 | Weil et al. | 600/16 |
| 5,216,032 | 6/1993 | Manning | 514/718 |
| 5,334,142 | 8/1994 | Paradis | 604/53 |
| 5,449,342 | 9/1995 | Hirose et al. | 600/16 |

FOREIGN PATENT DOCUMENTS

1076119 A  2/1984  U.S.S.R.

OTHER PUBLICATIONS

H. Memezawa et al., Effects of Fluosol–DA on Brain Edema, Energy Metabolites, and Tissue Oxygen Content in Acute Cerebral Ischemia, *Advances in Neurology*, vol. 52, pp. 109–117 (1990).

Emerman, et al., Hemodynamic Effects of the Intra–aortic Balloon Pump During Experimental Cardiac Arrest, *Am. J. Emerg. Med.*, vol. 7, pp. 378–383 (1989).

Cleman, et al., Prevention of ischemia during percutandous transluminal coronary angioplasty by transcatheter infusion of oxygenated Fluosol DA 20%, *Circulation*, vol. 74 (1986).

Becker, et al., Outcome of CPR in a Large Metropolitan Area—Where are the Survivors?, *Annals of Emergency Medicine*, pp. 355–361, (1991).

Bajaj, et al., Limitation of Myocardial Reperfusion Injury by Intravenous Perfluorochemicals, *Circulation*, vol. 79, pp. 645–656 (1989).

*The Merck Index; An Encyclopedia of Chemicals, Drugs, and Biologicals*, pp. 392, 625, 933, 1131 (1989).

Martin, et al., Aortic and Right Atrial Pressures During Standard and Simultaneous Compression and Ventilation CPR in Human Beings, pp. 125–130, (1986).

Hoffman et al., Digitalis and Allied Cardiac Glycosides, *Goodman and Gilman's The Pharmacological Basis of Therapeutics*, pp. 716–718, (1985).

Novick, et al., Protection of the hypertrophied pig myocardium, *Cardiovasc Surg*, vol. 89, pp. 547–566 (1985).

Martin et al., *Physical Pharmacy*, Third Edition, pp. 276–277, (1983).

Primary Examiner—John P. Lacyk
Attorney, Agent, or Firm—Myers Bigel Sibley & Sajovec, LLP

[57] ABSTRACT

A method of treating a subject in cardiac arrest comprises the steps of blocking the descending aorta of the subject and perfusing the aortic arch of the subject with a protective solution in an amount effective to deliver oxygen to the heart of the subject. The perfusing step is performed so that the protective solution infuses the aorta in a pulsatile rhythm. An apparatus for carrying out this method includes a storage unit for storing a protective solution, delivery apparatus for delivering the protective solution to the aorta of the subject, wherein the delivery apparatus is fluidly connected with said storage means, and a pulsing device connected with the delivery means. The pulsing device induces the protective solution to be delivered to the aorta in a pulsatile rhythm.

13 Claims, 6 Drawing Sheets

METHOD OF TREATING CARDIAC ARREST AND APPARATUS FOR SAME

FIELD OF THE INVENTION

The present invention relates generally to a method of treating patients in cardiac arrest, and more particularly relates to a method of treating cardiac arrest patients through selective aortic arch perfusion.

BACKGROUND OF THE INVENTION

When a person suffers a cardiac arrest, whether it be inside a hospital or elsewhere, the survival rate is relatively low. See L. Becker et al., Ann. Emerg. Med. 20, 355–361 (1991). One of the reasons for the high mortality rate is that cardiopulmonary resuscitation (CPR), one of the primary resuscitation methods, induces little forward blood flow. Although certain drugs, such as epinephrine, can improve vital organ blood flow during CPR, these drugs are administered almost exclusively into a vein; as such, the drug must circulate to and through the heart and lungs before arriving at the peripheral arteries where their primary beneficial pharmacological effects occur. During this low blood state of CPR, the heart and brain receive very limited blood flow blood that may fail to sustain cellular survival.

Invasive techniques such as open-chest cardiac massage (OCCM), direct mechanical ventricular assistance (DMVA), and cardiopulmonary bypass (CPB) can provide better vital organ blood flow. See generally R. Bartlett et al., Ann. Emerg. Med. 13 (Part 2), 773–777 (1984); M. Anstadt et al., Resuscitation 21, 7–23 (1991); P. Safar et al., Am. J. Emerg. Med. 8, 55–67 (1990). However, adaptation of these techniques for widespread use, particularly in a setting outside a hospital, is unrealistic. In most cases, the response time that would enable significant neurologic recovery would likely run out before these techniques could be employed in a typical emergency.

Selective aortic arch perfusion (SAAP) is a technique designed to provide relatively isolated perfusion of the heart and brain in patients suffering cardiac arrest. SAAP is typically performed by inserting a large lumen balloon occlusion catheter, percutaneously or by surgical cutdown, into a femoral artery and then advancing the catheter tip to the descending aortic arch, preferably just distal to the left subclavian artery. With the SAAP catheter balloon inflated to prevent or restrict distal aortic flow, the coronary and cerebral circulations can be relatively selectively perfused with a solution infused via the lumen of the SAAP catheter. The infused solution is typically an oxygenated blood substitute, such as a perfluoro carbon emulsion or polymerized hemoglobin solution, that contains various agents capable of reversing ischemic metabolic processes, restoring peripheral vascular resistance, correcting hemostatic derangements, and limiting reperfusion-induced cellular damage. For example, vasoconstrictors such as epinephrine are beneficial. Perfusion with such a solution can enhance return of spontaneous cardiac function and facilitate neuronal functional recovery. This technique is described in some detail in U.S. Pat. No. 5,216,032 to Manning.

Research has indicated that, although SAAP shows promise, the technique has certain shortcomings. For example, U.S. Pat. No. 5,216,032 to Manning (discussed above) indicates that SAAP is more effective if the aortic valve remains closed. Manning suggests that an initial rapid infusion bolus be administered to close the aortic valve consistently. However, if SAAP is combined with CPR or some other chest-compressing treatment, the aortic valve can open, thereby resulting in aortic-to-left ventricular shunting of SAAP infusate. This can lead to decreased coronary perfusion and even pulmonary congestion. Another shortcoming of SAAP is due to the so-called "no-reflow" phenomenon, in which certain areas of the cerebral and coronary vascular beds are obstructed due to microvascular sludging of blood cells and perivascular edema. These processes in the microvasculature can prevent blood flow therein even when circulation has been restored. The prior art is silent regarding solutions addressing these shortcomings.

SUMMARY OF THE INVENTION

The present invention responds to the aforementioned shortcomings. As a first aspect, the present invention includes a method of treating a subject in cardiac arrest that comprises the steps of blocking the descending aorta of the subject and perfusing the aortic arch of the subject with a protective solution in an amount effective to deliver oxygen to the heart of the subject. The perfusing step is performed so that the protective solution infuses the aorta in a pulsatile rhythm. Perfusion in a pulsatile rhythm can more effectively flush the subject's microvasculature of sludged blood vessels and overcome perivascular edema, thereby improving the flow of the protective solution.

If performed during CPR, it is preferred that the pulsatile rhythm is selected and timed so that the infusion pulses of protective solution occur during the decompression or relaxation phase of CPR, as this ensures that the aortic valve is closed and thus prevents backflow of protective solution into the heart from the aorta. It is also preferred that the pulsatile rhythm be selected to resemble a pulse rate that coincides with normal cardiac function.

The present invention also includes an apparatus for treating a subject in cardiac arrest. The apparatus comprises storage means for storing a protective solution, delivery means for delivering the protective solution to the aorta of the subject, wherein the delivery means is fluidly connected with said storage means, and pulsing means connected with the delivery means. The pulsing means induces the protective solution to be delivered to the aorta in a pulsatile rhythm. Preferably, the apparatus includes means for delivering either a protective solution or autologous blood to the subject, and further includes means for controlling the pulsatile rhythm so the perfusion occurs during the decompression or relaxation phase of CPR.

DETAILED DESCRIPTION OF THE INVENTION

The present invention will now be described hereinafter in detail with reference to the accompanying drawings. The present invention is not, however, limited to the embodiments described herein; rather, these embodiments are intended to enable those skilled in this art to understand fully the invention.

As described above, the present invention is directed to methods and associated apparatus for treating a subject in cardiac arrest. As used herein, the term "cardiac arrest" refers to all types of cardiac arrest, including ventricular fibrillation, asystole, and pulseless electrical activity. The subject of such cardiac arrest is preferably mammalian and more preferably human, but can be any animal that can be advantageously treated by oxygenating its brain and coronary vasculature during cardiac arrest.

Figure 1:
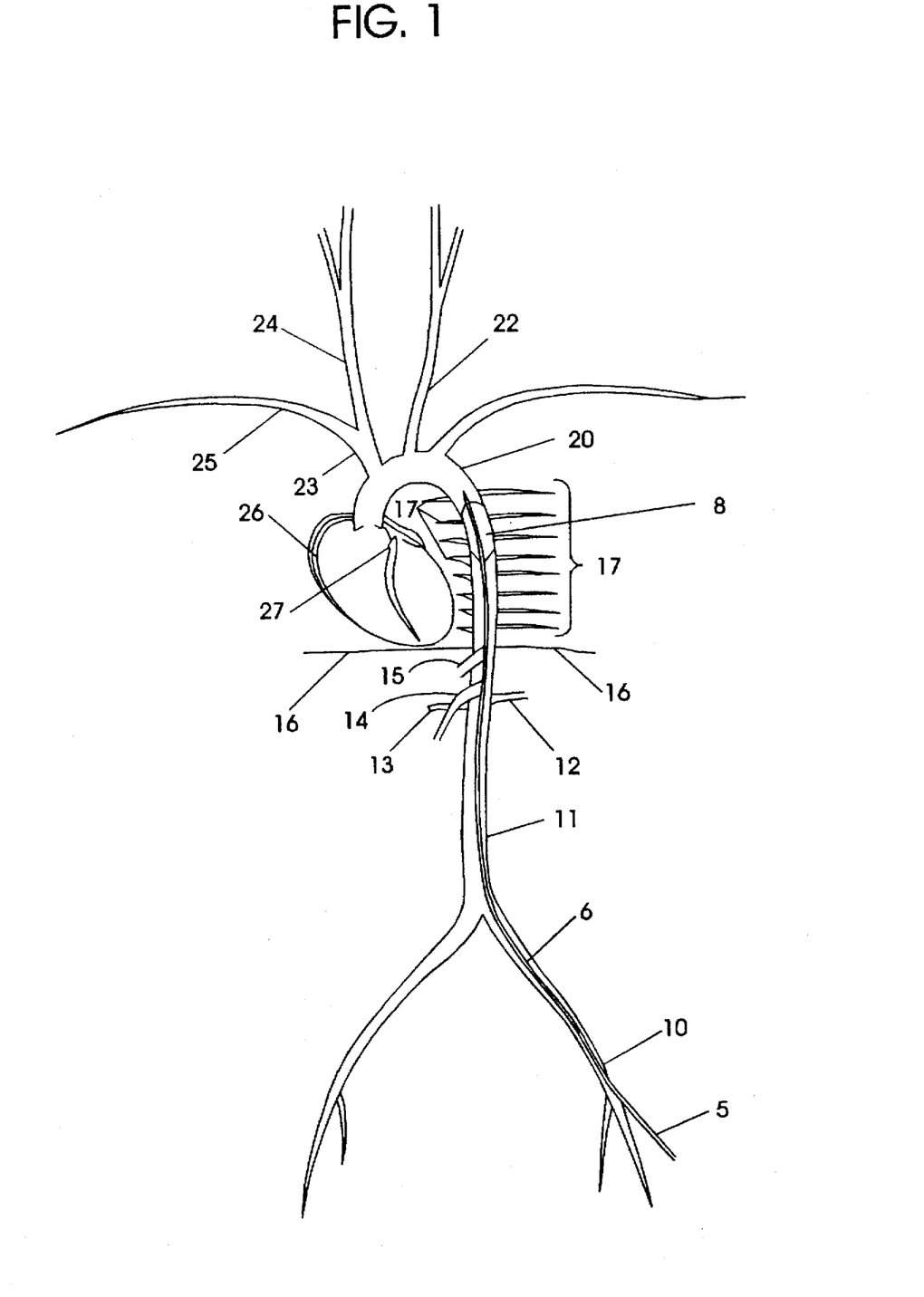
FIG. 1 is a schematic illustration of a balloon catheter inserted through the femoral artery into the aorta in a human subject proximal to the diaphragm but distal to the left subclavian artery, with the balloon inflated to block the descending aorta.
Figure 2:
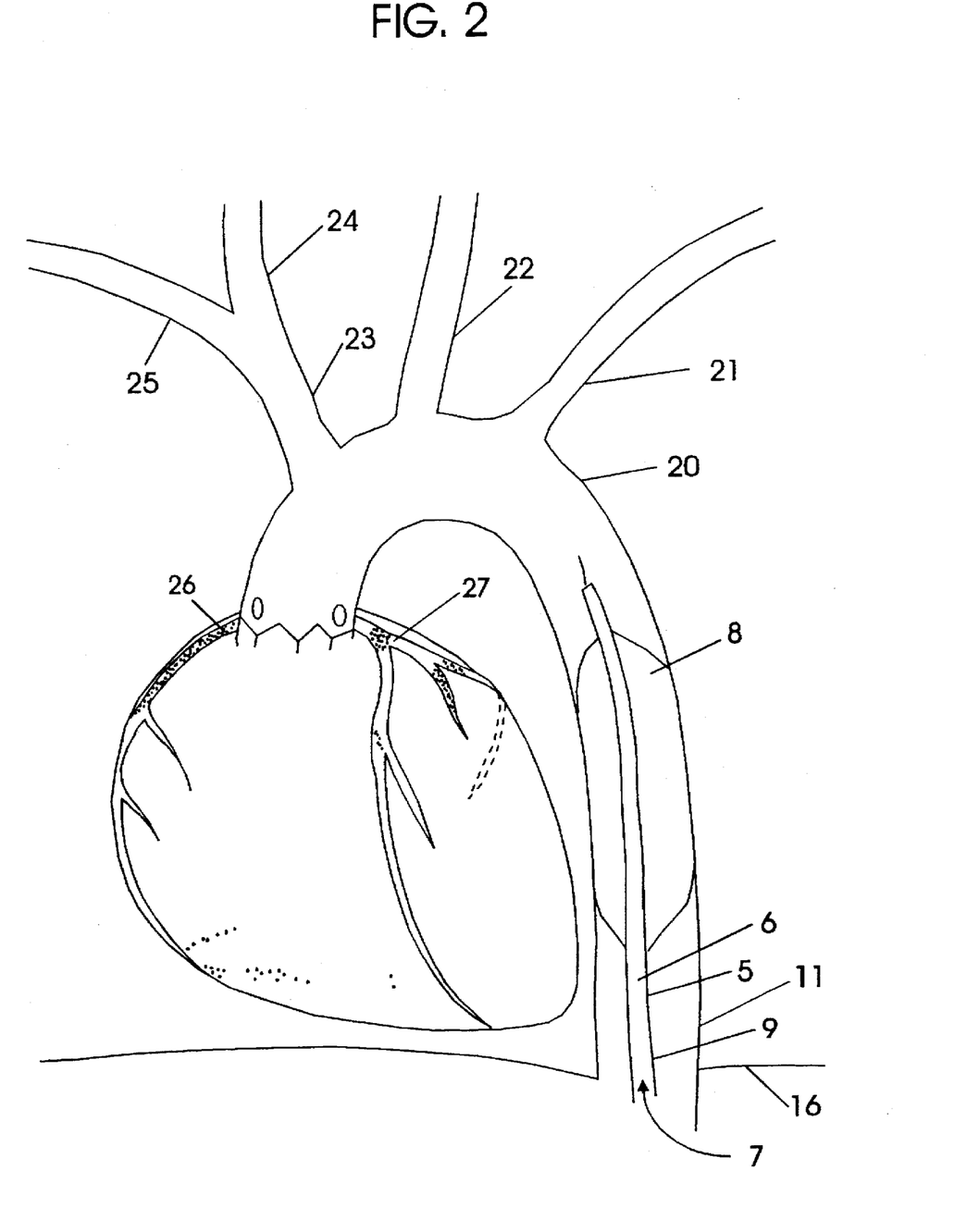
FIG. 2 is an enlarged partial view of the heart and balloon catheter of FIG. 1 showing the balloon catheter positioned to block the descending aorta and perfuse the aortic arch.

Blocking of the descending aorta, and infusion into the aortic arch, is preferably carried out with a balloon catheter unit such as that illustrated at 5 in FIGS. 1 and 2. The balloon catheter unit 5 comprises an elongate catheter tube 6 having a primary lumen 7 through which protective solution may pass, and further comprises a balloon 8 at one end of the elongate tube 6 configured to be inflated to block the descending aorta of a human subject. A secondary tube 9 (or alternatively a secondary lumen formed in the wall of the tube 6 and extending longitudinally therewith) provides a mechanism for inflating the balloon 8 once the balloon 8 is positioned in the desired location within the descending aorta of the subject. A connector such as a Leur Lock™ fitting is provided at the end of the elongate tube 6 opposite the balloon 8 to connect the catheter tube 6 to a supply of the protective solution.

For a human adult, the size of the primary lumen 7 may be from 6 French to 14 French, the length of the catheter tube 6 may be from 50 to 150 centimeters, the inflated dimensions of the balloon 8 may be from 1.5 to 4 centimeters in diameter, the length of the balloon 8 may be from 2 to 10 centimeters, and the distance from the tip of the catheter tube 6 to the balloon 8 distance may be from 1 to 4 centimeters. For a human child, the lumen size may be from 5 French to 10 French, the catheter tube length may be from 20 to 80 cm, the balloon inflated dimensions may be from 0.75 to 2 cm in diameter, the balloon length may be 1.5 to 6 cm, and the catheter-tip to balloon distance may be from 0.5 to 2 cm. When inflated, the balloon 5 should be capable of withstanding a pressure of at least 300 to 500 mmHg to prevent leakage of protective solution down the descending aorta and rupture of the balloon during chest compression.

The catheter tube 6 may be made from a firm but somewhat flexible plastic material, and the balloon 8 from a latex or polyurethane material. The catheter tube 6 may be made from antithrombotic materials, such as having heparin bonding as a characteristic of construction, to inhibit formation of blood clots in the aorta. Reference may be made to U.S. Pat. Nos. 5,049,132; 5,049,131; 5,045,061; 5,042,976; 5,041,125; and 5,216,032 for further guidance in the construction of the balloon catheter. It is specifically intended that the disclosures of all patent references cited herein be incorporated herein by reference.

To block the descending aorta of the subject (FIGS. 1 and 2), the balloon catheter unit 5 is inserted into a femoral artery 10 of the subject and advanced within the descending aorta 11 past the renal arteries 12, 13, the superior mesenteric artery 14, the celiac trunk 15, the diaphragm 16, and past various ones of the intercostal arteries 17. The balloon 8 is preferably positioned distal to the carotid arteries 22, 24 and the left subclavian artery 21, but is preferably located at least proximal to the renal arteries 12, 13. The balloon 8 is inflated via the secondary tube 9 to block the descending aorta 11, with the leading end of the elongate tube 6 positioned to perfuse the aortic arch 20. In this position, protective solution pumped or forced through the balloon catheter unit 5 and exiting the balloon 8 will perfuse the left subclavian artery 21, the left common carotid artery 22, the brachiocephalic trunk 23 (and in turn the right carotid artery 24 and the right subclavian artery 25) and the coronary arteries 26, 27. Although it is preferred to block the descending aorta with a balloon catheter as illustrated, those skilled in this art will appreciate that other means for blocking the descending aorta to prevent flow therein, such as manual aortic compression, can also be used with the present invention.

Perfusion of the aorta of the subject is carried out by infusing the aortic arch of the subject with protective solution. The protective solution is preferably an oxygen-carrying, or oxygenating, solution (i.e., a perfluorocarbon emulsion, a polymerized hemoglobin solution, a lactated Ringer's solution, or other blood substitute) optionally containing various other agents such as antioxidants, calcium channel blockers, iron chelators, metabolic substrates, adrenergic agents, antithrombotics, anticoagulants, and the like, in an amount to combat tissue reperfusion injury and/or enhance cardiac activity while protecting the brain until spontaneous circulation is restored. The solution may be a single phase solution, a dispersion, an emulsion, or any other form physically suitable for delivery to the tissue. The protective solution is "physiologically acceptable" in that it is suitable for injection into the subject without causing undue deleterious effects.

It is also anticipated that autologous blood of the subject may be used as the protective solution. This is particularly preferred when at least one perfusion has already been carried out; use of the subject's blood rather than a blood substitute reduces any adverse effects that can result from the infusion overload into the subject's circulatory system. Perfusion of autologous blood is discussed in detail in co-pending U.S. Patent Application entitled METHOD OF TREATING CARDIAC ARREST, filed concurrently.

Any physiologically acceptable blood-substitute solution may be employed in carrying out the invention. One example is Oxygent™, an intravascular perfluorocarbon emulsion comprised of up to 90 percent perfluorooctyl bromide and available from the Alliance Pharmaceutical Corp. San Diego, Calif. Aqueous emulsions containing fluorochemicals in high concentration are disclosed in U.S. Pat. Nos. 4,895,876 and 4,866,096; a liquid composition containing perfluorocyclocarbon and an organoamine oxide is disclosed in U.S. Pat. No. 4,443,480; a process for preparing stable emulsions of artificial blood containing perfluorocarbon compounds is disclosed in U.S. Pat. No. 4,497,829; liquid compositions containing fluorinated triethylenediamines are disclosed in U.S. Pat. No. 4,814,446.

The protective solution, whether a blood substitute or autologous blood, should be oxygenated prior to infusion. This can be carried out by contacting the protective solution with an oxygen-rich atmosphere such as Carbogen (95% $O_2$/5% $CO_2$). The protective solution may be administered at ambient temperature, or may be warmed to a temperature up to body temperature (37° Centigrade) prior to administration. The protective solution may further contain a vasoconstrictor, as discussed below.

Typically between about 250 to 3000 milliliters of the protective solution are infused, with 750 to 2000 milliliters of the protective solution being a more preferred dosage. Perfusion should be carried out sufficiently rapidly to enhance cardiac electrical activity; preferably, the perfusion duration is less than five minutes, and more preferably is less than one to two minutes. In general, the rate of infusion will be from 5 to 20 mL/kg/minute, and will most preferably be from 10 to 15 mL/kg/minute.

In accordance with the present invention, perfusion of the aortic arch is carried out in a pulsatile rhythm. As used herein, a "pulsatile rhythm" means that the protective solution is infused in a pulsating fashion, such that greater and lesser amounts of the protective solution are infused alternatively. Although the inventor does not wish to be bound by a theory of operation, it is hypothesized that a pulsatile infusion rhythm, particularly one that closely resembles or mimics the aortic pressure fluctuations of the normal cardiovascular state, can be more effective in delivering blood or a blood susbstitute to the brain and coronary arteries. In particular, a pulsatile rhythm may flush the microvasculature of sludged blood cells and overcome perivascular edema, which flushing can improve blood flow to the microvasculature. Also, the rheology of blood may be such that a pulsed infusion may be more effective in initiating the movement of pooled blood (in which blood cells may have agglomerated) than a continuous infusion.

During pulsatile perfusion, the pressure difference between the maximum and minimum pressures experienced by the aorta (i.e., the systolic and diastolic pressures) is typically between about 5 and 50 mm Hg, and more preferably is between about 20 and 40 mm Hg. The "pulsing cycle" (i.e., the duration between one maximum pressure infusion and the next separated by a pressure drop) is preferably between about 30 and 200, and more preferably between about 50 and 120, cycles per minute. Each of these infusion parameters (i.e., the rate of pulsatile infusion and the pressure experienced within the aorta) may be selected to substantially mimic or resemble normal cardiac function, as it is hypothesized that, due to the unique composition and rheology of blood, blood circulation may be improved if the blood is forced through the circulatory system by forces similar to that experienced during normal cardiac function Perfusion with a pulsatile rhythm can be carried out in conjunction with other resuscitation methods, such as CPR. If carried out in conjunction with CPR, pulsatile perfusion can be timed to occur during the diastolic (i.e., relaxed, or decompressed) phase of CPR. As noted above, CPR chest compressions can open the aortic valve and thereby cause aortic-to-left ventricular shunting of protective solution, which in addition to reducing coronary perfusion, can also lead to pulmonary congestion. If, however, perfusion is limited to those time periods between chest compressions, and is carried out with sufficient pressure, the aortic valve should remain shut, thus preventing such shunting of protective solution. Further, pulsed diastolic infusions can raise arterial pressure and coronary perfusion pressure, which together can improve coronary artery perfusion.

Pulsatile perfusion can be effected in any manner recognized by those skilled in this art to be suitable for delivering a substance in a pulsatile rhythm. Exemplary apparatus include rotary roller pumps, reciprocating syringe-type pumps, squeezable bulbs, and the like. It is preferred that the perfusion apparatus be operably controlled by a controller that is also operably connected to a CPR device so that the operation of each is coordinated.

It is also preferred that the pressure within the aorta be monitored during perfusion; this information can be used to adjust the infusion quantity, duration, or pressure. A controller operably connected to the pressure monitor and to the delivery system for the protective solution can be configured to automatically provide a preselected quantity of protective solution.

A vasoconstrictor may be employed in the methods described herein. Suitable adrenergic vasoconstrictors include epinephrine, norepinephrine, methoxamine, phenylephrine, with epinephrine being preferred; nonadrenergic vasoconstrictors can also be used. Vasoconstrictors may be administered by any suitable means, such as by parenteral injection (e.g., intravenous injection, intraarterial injection, subcutaneous injection, intramuscular injection, intraperitoneal injection, tracheobronchial administration), or by including the vasoconstrictor in the protective solution used to perfuse the aortic arch. It is preferred that the administration of the vasoconstrictor be concurrent with (i.e., sufficiently close in time to) perfusion of the aortic arch so that the vasoconstrictor will affect coronary perfusion with the protective solution. The dosage of the vasoconstrictor will vary depending on the subject and the particular vasoconstrictor chosen, but will generally be between 0.002 and 0.3 mg/kg, will more preferably be between 0.005 and 0.2 mg/kg, and will most preferably be between 0.01 and 0.1 mg/kg.

Medicaments containing a vasoconstrictor for enhancing coronary perfusion with a protective solution during selective aortic arch perfusion may be prepared by contacting and mixing the vasoconstrictor with a pharmaceutically acceptable carrier, such as a sterile pyrogen-free saline solution, in accordance with techniques known in the pharmacy art. The pharmaceutical carrier may be the protective solution itself, such as a perfluorochemical blood-substitute solution as discussed above.

Restoring spontaneous circulation in the subject may be carried out by any suitable means, such as electric shock or precordial thump (i.e., application of an external force), or by enhancing electrical activity through perfusion and other resuscitation techniques so that normal electrical activity re-emerges without application of an external force. An electric shock to heart muscle tissue which will restore spontaneous circulation from a chaotic electrical signal (or "defibrillation") may be administered with any suitable defibrillator, such as the Responder™ 1500 (manufactured by Marquette Electronics, Milwaukee, Wis.). As discussed above, it is preferred that a mechanical CPR device be operably coupled with the perfusion unit so that infusion can occur during a decompression phase of CPR.

Figure 3:
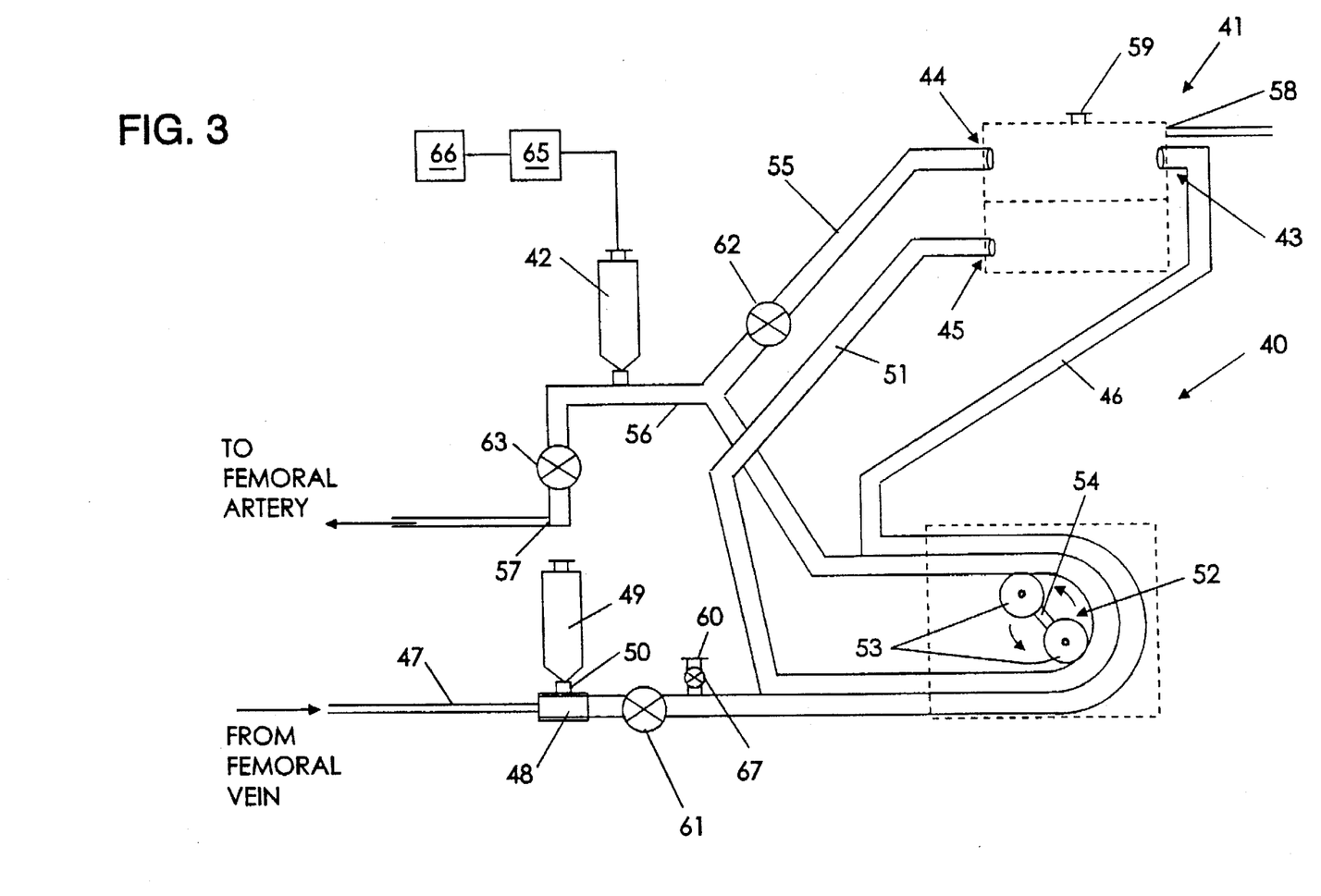
FIG. 3 is a schematic illustration of an exemplary SAAP system and its catheter extending into the femoral artery of a subject.

An exemplary SAAP apparatus 40 is schematically illustrated in FIG. 3. The apparatus 40 comprises an oxygenating storage tank 41 having two upper ports 43, 44, and a lower port 45. A venous blood withdrawal line 46 is attached at one end to upper port 43 and at its other end to a venous blood withdrawal catheter 47 by a fitting 48. The venous blood withdrawal catheter 47 is to be inserted into the femoral vein of a subject. An anticoagulant syringe 49 is also fluidly connected to the fitting 48 via a catheter, connector, or connecting tubing 50. An oxygenated blood infusion line 51 is attached at one end to the lower port 45. As the oxygenated blood infusion line 51 extends away from the lower port 45, it meets with and travels adjacent to the venous blood withdrawal line 46. The adjacent sections of the lines 46, 51 are enclosed within a roller pump apparatus 52, which comprises a pair of wheels 53 mounted on a rotary arm 54. Rotation of the arm 54 causes the wheels 53 to contact the lines 46, 51 and thereby deliver blood or a blood substitute to and from the SAAP apparatus 40. At its outlet end, the oxygenated blood infusion line 51 meets the outlet end of an oxygenated blood recirculation line 55 that extends thereto from the upper port 44. An infusion line 56 extends from the junction of the lines 51, 55 to an infusion port 57 that is connected to the inlet end of a balloon catheter (not shown) that is to be inserted in the femoral artery of a subject. A syringe 42 is fluidly interconnected with the infusion line 56. The storage tank 41 also includes an oxygen intake port 58 and an additional syringe port 59. The venous blood withdrawal line 46 also includes an oxygen intake port 60 between the fitting 48 and the roller pump apparatus 52. Three valves 61, 62, 63 are located, respectively, adjacent the fitting 48 on the venous blood withdrawal line 46, on the oxygenated blood recirculation line 55, and on the infusion line 56 between the syringe 42 and the infusion port 57. A fourth valve 67 is located on the oxygen intake port 60. A controller 65 is operably connected with the syringe 42 to control its operation and is also operably connected with a CPR device (indicated schematically at 66). The apparatus 40 may also include a valve (not shown) that can remove any air that enters the system prior to its being introduced into the subject's aorta.

In operation, autologous blood is drawn from the subject into the femoral venous blood withdrawal catheter 47. Anticoagulant, such as heparin, is added to the withdrawn blood through the anticoagulant syringe 49. The venous blood is pumped through the venous blood withdrawal line 46 by the roller pump apparatus 52; as the rotary arm 54 rotates, the wheels 53 provide a positive pressure on the blood that forces it through the line 46. The venous blood enters the storage tank 41 through upper port 43 and flows into the bottom portion of the storage tank 41. Oxygen is continuously introduced into the storage tank through the oxygen intake port 58. After the blood is oxygenated in the storage tank 41, it flows therefrom through the lower port 45 into the oxygenated blood infusion line 51. The blood is propelled by the action of the roller pump unit 52 to the infusion line 56. Flow into the oxygenated blood recirculation line 55 is prevented because the valve 62 is in a closed position. Oxygenated blood can be furnished in a pulsatile rhythm by reciprocating action from the syringe 42. The oxygenated blood flows through the infusion line 56, through the infusion port 57, and into the balloon catheter for delivery to the aorta.

Similarly, this apparatus 40 can also be used to deliver a blood substitute to the subject. The blood substitute can be introduced into the storage tank 41 through the syringe port 59. The valves 61 and 62 are in their closed positions. Protective solution follows the same path to the subject as that of oxygenated blood described above.

Further, the apparatus 40 can be used to recirculate, and thereby thermally and hemodynamically prepare, protective solution for perfusion. For recirculation of protective solution, valve 63 is in its closed position, and valve 62 is in its open position. This creates a closed loop system that proceeds from the storage tank 41 to the oxygenated blood infusion line 51, the recirculation line 55, and the upper port 44 before returning to the storage tank 41.

Use of the apparatus 40 is exemplified by the following scenario. A physician arrives at the scene of a cardiac arrest patient and secures access to the femoral artery by either percutaneous or surgical means. The blood substitute solution is oxygenated during the vascular access procedure. The balloon catheter is advanced to the thoracic aorta and epinephrine is administered into the aortic arch. The catheter balloon is inflated and an initial SAAP infusion of the blood substitute (which can contain reperfusion-injury combating agents) is performed. An initial bolus of blood substitute is rapidly infused to close the aortic valve and CPR is halted for the initial infusion lasting 30 to 60 seconds. This would assure that the myocardium was effectively perfused with the blood substitute. During this initial infusion, access to a femoral vein is secured. Aortic arch epinephrine administration can be titrated to maximize CPR-diastolic coronary perfusion pressure (CPP). Two to three minutes after the initiation of the first blood substitute infusion, a second blood substitute infusion is initiated. Pulsed diastolic infusion induced by the syringe 42 using half of the volume initially infused would be used to elevate CPP and diminish the volume effects of a second infusion. The infusion pulses are administered during the decompression and relaxation phases of CPR. During the second blood substitute infusion, femoral blood is withdrawn, anticoagulated via the anticoagulant syringe, oxygenated in the storage tank 41, thermally treated (if necessary), and filtered in preparation for reinfusion. Depending upon the rapidity of femoral venous access and blood withdrawal, either a third blood substitute infusion similar to the second or an autologous blood infusion is initiated. Aortic arch epinephrine titration, other pharmacologic therapies, and repetitive or continuous autologous blood SAAP can be performed until return of spontaneous circulation (ROSC) is attained or the resuscitative efforts are halted. If ROSC is attained, autologous blood withdrawal and reinfusion could be continued (with or without the catheter balloon inflated depending on the clinical situation) serving as partial cardiopulmonary bypass support for the still unstable cardiovascular system in the early post-resuscitation phase. Graded balloon inflation could be used to provide peripheral resistance as needed in the immediate and early post-resuscitation phase.

Figure 4:
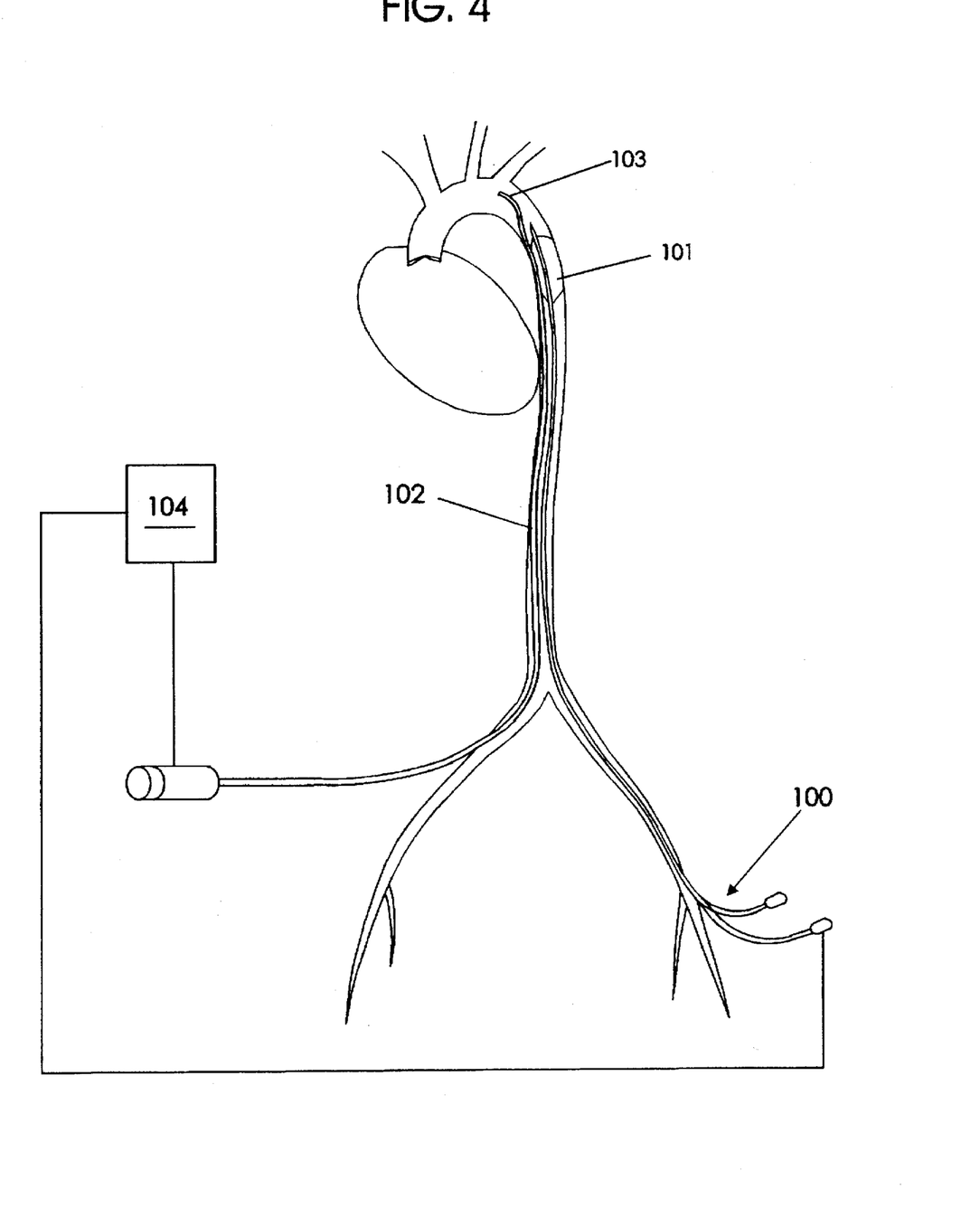
FIG. 4 is a schematic illustration of a balloon catheter and a micromanometer catheter inserted into the femoral artery of a subject.
Figure 5:
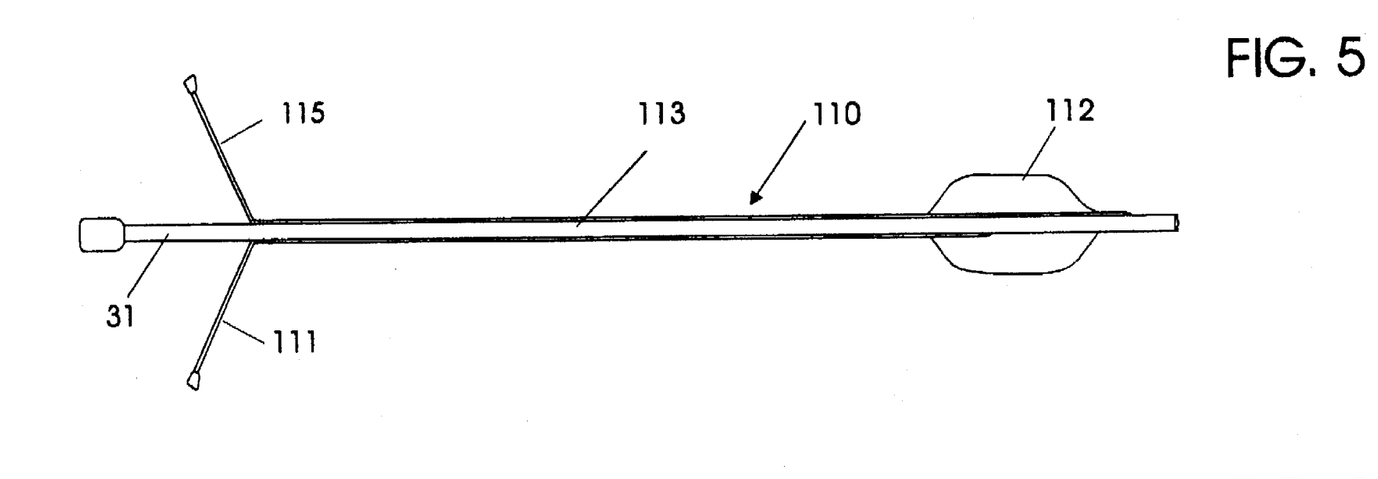
FIG. 5 is a schematic illustration of a triple lumen SAAP catheter.
Figure 6:
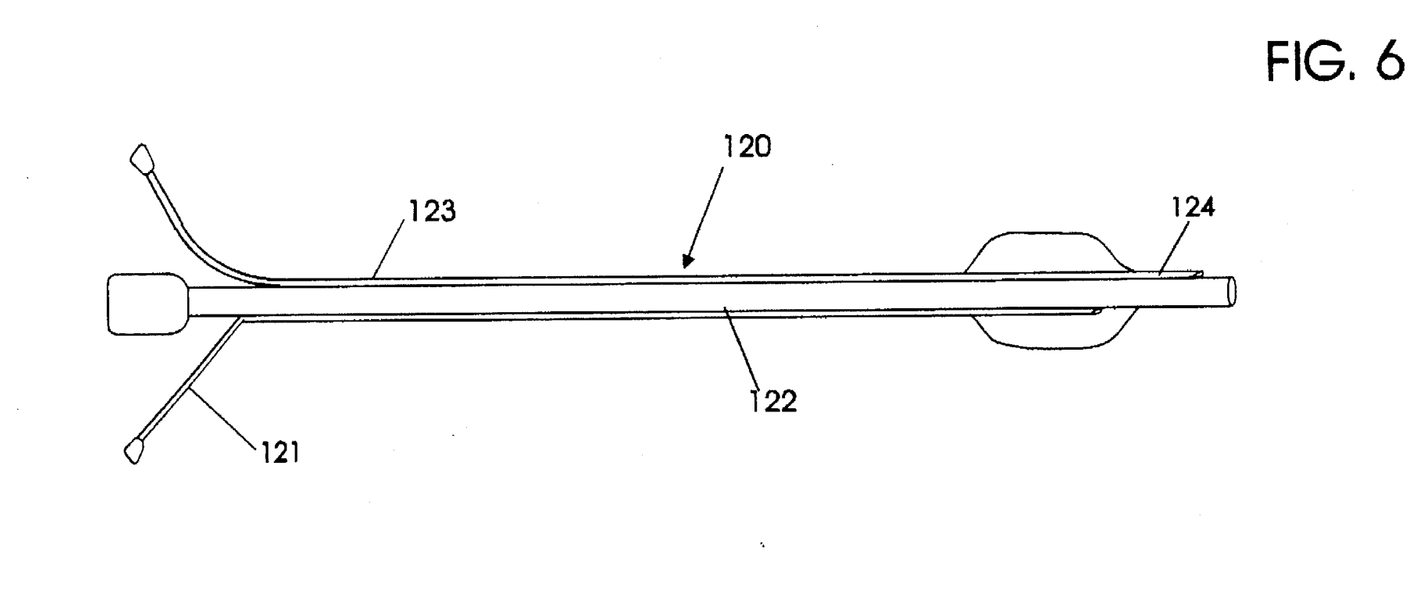
FIG. 6 is a schematic illustration of a double lumen SAAP catheter with an attached micromanometer transducer.

As noted above, it can be beneficial to monitor the pressure within the aorta during infusion, particularly when a pulsatile infusion rhythm is employed, and more particularly when the pulses of the infusion are timed to occur during chest decompressions of CPR (i.e., CPR-diastolic pulses). FIGS. 4, 5 and 6 schematically illustrate three different catheter embodiments that enable the pressure to be monitored. FIG. 4 illustrates a balloon catheter 100 that is inserted within the aorta adjacent a micromanometer-tipped catheter 102. The micromanometer tip 103 of the catheter 102 is positioned above (i.e., nearer the heart) the balloon 101 of the catheter 100 to enable the pressure at that location to be monitored. Preferably and illustratively, the catheter 102 is operably connected to a controller 104 that is also operably connected to a mechanical CPR unit (not shown) and to a perfusion system connected to the balloon catheter 100. When the pressure detected by the micromanometer tip 103 falls below a predetermined level, thereby indicating that the CPR unit is in decompression or relaxation phase (as opposed to a chest compression phase) and thus it is desirable that the aortic valve be closed, the controller 104 activates the perfusion system to infuse a protective solution pulse. At higher pressures experienced during chest compression, the controller 104 prevents infusion to avoid misdirecting protective solution into the left ventricle.

FIG. 5 schematically illustrates another pressure-detecting catheter embodiment. A triple-lumen catheter unit 110 comprises three separate channels: a balloon inflation line 111 that terminates within the balloon 112 of the unit 110; an infusion line 113 that terminates beyond the balloon 112 to provide protective solution; and a fluid-filled pressure monitoring line 115 that also terminates beyond the balloon 112. Another embodiment, illustrated in FIG. 6, is a double-lumen catheter 120 having the typical balloon inflation line 121 and infusion line 122, but also including an electrical line 123 tipped with a pressure transducer 124 located beyond the balloon. Each of the embodiments of FIGS. 5 and 6 can be operated in a similar manner to the embodiment of FIG. 4.

The present invention may be beneficial in the management of traumatic and other nontraumatic/surgical causes of cardiac arrest or profound hypovolemia with impending cardiac arrest. In addition to rapid volume replacement, the catheter balloon could serve much like an aortic cross-clamp to significantly reduce or stop exsanguinating hemorrhage from the abdomen, pelvis, or lower extremities until the patient can be transferred to the operating room. Clinical situations where the present invention can be used include: blunt abdominal or multi-system trauma with profound hemorrhage/hypovolemia; penetrating abdominal trauma with profound hemorrhage/hypovolemia; ruptured abdominal aortic aneurysm with profound hypotension or impending arrest; and major pelvis fractures or disruption.

The invention is disclosed in greater detail in the following non-limiting examples. In the examples, "kg" means kilograms, "mg" means milligrams, "mmHg" means pressure measured in millimeters of mercury, "°C." means degrees Celsius, "Fr" means lumen diameter measured in French, "mL" means milliliters, "mEq" means milliequivalents, "Hz" means Hertz, "cm" means centimeters, "J" means joules, "min" means minutes, "sec" means seconds, and "w/v" means weight per unit volume.

EXAMPLE 1

Animal Model of Cardiac Arrest

The canine cardiac arrest model described in this section was used for all of the SAAP studies subsequently described. Differences in the protocols between experimental studies are described under the individual study sections.

Animals: Mongrel canines from a single provider source were used in all of the SAAP studies. Animals were evaluated by the staff of the Division of Laboratory Animal Medicine for evidence of acute or chronic illness.

Anesthesia: Anesthesia was induced with thiopental 25–30 mg/kg IV and maintained with inhalational enflurane at 1.5% using a volume ventilator at an $F_1O_2$ of 0.21. End-tidal $CO_2$ was continuously measured with a sidestream sampling capnometer (Datex) and minute ventilation was adjusted to an end-tidal $CO_2$ of 38–42 mmHg. ECG lead II was monitored. Body temperature was maintained at 37°–38° C. with a warming blanket. Arterial blood gases were obtained to assure normal acid-base status. Ventilatory adjustments were made as needed to adjust the arterial pH to the 7.30–7.40 range. Serial evaluation of reflexes, heart rate and responses to graded pain stimulation were performed to assure adequate anesthesia.

Instrumentation: Catheter introducers (8.5 Fr) were placed percutaneously into the right and left external jugular veins. Surgical cutdowns were performed to expose the right and left femoral vessels. Fluoroscopy was used to position all catheters. A Swan-Ganz catheter and a pacing wire were inserted via the external jugular veins into a pulmonary artery and the right ventricle, respectively. Micromanometer-tipped catheters (Millar Instruments) were positioned via the right femoral vessels into the right atrium and mid-aortic arch. A 9 Fr balloon occlusion catheter was inserted into the left femoral artery and advanced to the descending aortic arch. A 9 Fr catheter introducer was placed in the left femoral vein in animals undergoing blood withdrawal for subsequent reinfusion. A low pressure saline-filled balloon catheter was placed in the retrocardiac esophagus with a micromanometer catheter inside the balloon to measure esophageal pressure. Esophageal pressure served as an extravascular indicator of intrathoracic pressure changes during CPR. ECG and all pressures were continuously recorded on a multi-channel analog recorder (Grass Instruments Model 7 Polygraph).

Selective Aortic Arch Perfusion System: The major components of the SAAP system were: (1) a 9 Fr aortic arch balloon occlusion catheter; (2) a resuscitation solution; (3) an infusion pump; and (4) an oxygenation apparatus. Perfluorooctyl bromide emulsion (perflubron emulsion, [Oxygent™, Alliance Pharmaceutical Corporation, San Diego]) in a 60% weight/volume preparation was the resuscitation solution used in all studies evaluating pulsatile SAAP. Autologous blood was withdrawn and reinfused by the SAAP technique after initial perflubron infusion in the procedure described in Example 4 and as the only SAAP perfusate in the procedure described in Example 3. The infusion pump used was a Sarns low-pressure bypass pumphead. Pulsed infusion during SAAP was created using a 50 mL syringe connected to the infusion tubing between the Sarns pump and the SAAP catheter. The syringe was cyclically filled and emptied manually with approximately 10 mL of infusate withdrawn and then infused under maximal manual pressure at a rate of 60–80 pulsed infusions per minute. During the syringe withdrawal phase, all infusate from the Sarns pump was directed into the 50 mL syringe and, therefore, essentially no infusion through the SAAP catheter occurred during this phase. During the syringe emptying (infusion) phase, perfusate from both the syringe and the pump were permitted to flow out of the SAAP catheter. The total volume infused per infusion pulse was approximately 10 mL.

Perflubron emulsion was oxygenated with 100% oxygen to yield a $pO_2$ in the range of 730–790 mmHg. Sodium bicarbonate 3.0–4.0 mEq was added to each 300 mL volume of 60% w/v perflubron emulsion in order to yield a pH of 7.35–7.45. The $pCO_2$ with this preparation was less than 10 mmHg. Temperature was adjusted to 37° C.

In the two procedures using autologous blood (Examples 3 and 4), femoral venous blood was withdrawn, heparinized, circulated through the oxygenator, maintained at 37° C. and then reinfused via the SAAP catheter at time intervals described in the individual study sections.

The SAAP catheter latex balloon was inflated sufficiently to completely occlude the aorta just prior to SAAP infusion and the Sarns pump was used to infuse the perflubron and/or autologous blood. For all SAAP infusions used in the SAAP studies, an initial 50 mL bolus was rapidly infused in order to competently close the aortic valve. After the initial bolus, an infusion was maintained using the Sarns low-pressure bypass pumphead for a prescribed time interval.

Protocol—Baseline measurements of heart rate, aortic pressure, right atrial pressure, cardiac output, hematocrit, respiratory rate, tidal volume, end-tidal $CO_2$ arterial blood gases, and mixed venous blood gases were obtained before cardiac arrest. Ventricular fibrillation was induced using alternating current (60 Hz) applied to the heart for 3–5 seconds via the right ventricular pacing wire. Ventilatory support simultaneously ceased and the animals remained in ventricular fibrillation and total circulatory arrest for ten minutes. At the ten minute mark, mechanical CPR (Thumper™, Michigan Instruments) was initiated at a rate of 80 compressions of 130 lb per minute with animals in the supine position. Unless otherwise indicated, CPR was accompanied by epinephrine dosages of 0.01 mg/kg given intravenously. Ventilation was performed using 100% $O_2$ and inspiratory force of 25 cm $H_2O$ at a 5:1 compression-:ventilation ratio.

Experimental Therapeutic Interventions—Experimental interventions were initiated at 12 minutes after arrest. In all of the SAAP studies, defibrillation (electrical countershock) was attempted at one minute intervals as indicated after the experimental interventions were begun; defibrillation energy was applied at 100 J for the first defibrillation attempt, 150 J for the second, and 200 J for all others. Resuscitative efforts were continued as needed up to the 30 minute mark after initiation of ventricular fibrillation.

EXAMPLE 2

Serial SAAP-Perflubron Infusion Study

It was hypothesized that serial SAAP infusions would be more effective than a single brief SAAP infusion so long as volume overload effects could be avoided. It was also hypothesized that serial SAAP combined with aortic arch epinephrine administration would enhance ROSC compared to standard therapy in a model of ventricular fibrillation cardiac arrest. It was further hypothesized that SAAP performed as a pulsed infusion during CPR-diastole would diminish aortic valve regurgitation and that aortic pressures might be higher than those seen with continuous SAAP infusion without CPR. Thus, initial continuous SAAP without CPR (SAAP-C) was followed by pulsed diastolic SAAP during CPR (SAAP-PD) and the hemodynamic effects of the two methods were observed.

There were two intervention groups. The animals of the control group (n=6) received standard therapy with all epinephrine doses of 0.01 mg/kg given at 3 min. intervals via a peripheral forelimb intravenous (IV) catheter beginning at 12 min. of arrest. The animals of the experimental group (n=6) received standard therapy and aortic arch epinephrine (0.01 mg/kg given at 3 min. intervals) beginning at 12 min. of arrest. A first SAAP infusion with 300 mL of oxygenated 60% w/v perflubron emulsion began at 12 min 15 sec of arrest (50 mL bolus followed by a constant infusion over 30 sec) [SAAP-C]. CPR was halted during the first SAAP infusion. If needed, two more SAAP infusions were performed at 15 min 30 sec and 18 min 30 sec as CPR was continued (each was 150 mL of perflubron infused as 5–10 pulses during CPR-diastole)[SAAP-PD]

TABLE 1

| | | | CPP (Aortic pressure minus right atrial pressure) | | | | |
|---|---|---|---|---|---|---|---|
| Group | ROSC | 12 min | SAAP-C | 13 min | 15 min | SAAP-PD | 16 min |
| Control | 0/6 | 82 ± 3.1 | 8.3 ± 4.1 | 12.3 ± 6.7 | 12.8 ± 4.7 | 10.5 ± 3.7 | 10.2 ± 4.0 |
| SAAP | 4/6* | 7.5 ± 4.6 | 44.8 ± 13.8# | 17.3 ± 10.4 | 13.2 ± 9.0 | 48.5 ± 16.6# | 36.8 ± 37.1 |

*p < 0.05 vs Control Fisher's Exact
p < 0.01 vs Control, ANOVA

As the data indicates, ROSC was significantly increased by the combination of serial SAAP infusions and aortic arch epinephrine administration. CPP was substantially increased with both continuous SAAP and pulsed diastolic SAAP. SAAP-C and SAAP-PD appeared to have similar hemodynamic effects. However, coronary perfusion during SAAP-PD was not seen fluoroscopically as with SAAP-C.

EXAMPLE 3

Serial Pulsed Diastolic SAAP-Autologous Blood Study

SAAP using only autologous blood (AB) was studied to determined if this intervention alone might improve resuscitation outcome. The pulsed CPR-diastolic SAAP infusion method was used for this study.

There were two intervention groups. The animals in the control group (n=5) received standard therapy with the exception that all epinephrine doses of 0.01 mg/kg were given at 3 min intervals via the aortic arch beginning at 12 min of arrest. The animals of the experimental group (n=5) received CPR and aortic arch epinephrine as in the control group. At the 11 min mark, left femoral venous blood withdrawal began. SAAP-PD with autologous blood began at 12 min 15 sec and was continued 45 sec while CPR was in progress. PD-AB-SAAP infusion was repeated at 2 min intervals as needed until ROSC. The results of this procedure are shown in Table 2 below.

TABLE 2

| | | CPR-diastolic CPP (mmHg, mean ± S.D.) | | | | | |
|---|---|---|---|---|---|---|---|
| Group | ROSC | 11 min | 12 min | 13 min | 14 min | 15 min | 16 min |
| Control | 1/5 | 8.8 ± 2.4 | 9.0 ± 2.9 | 19.8 ± 9.2 | 16.0 ± 6.3 | 14.0 ± 6.3 | 11.5 ± 5.3 |
| PD-AS-SAAP | 5/5* | 9.6 ± 4.4 | 7.6 ± 5.8 | 45.8 ± 11.3# | 13.0 ± 10.3 | 38.0 ± 13.6# | 16.8 ± 9.9 |

*p < 0.05 vs Control, Fisher's Exact
p < 0.05 vs Control, ANOVA

As indicated by the data, PD-AB-SAAP increased ROSC and CPP significantly compared with standard therapy plus aortic arch epinephrine. As PD-AB-SAAP does not result in progressive volume loading, the procedure can be repeated continuously until ROSC is attained or resuscitative efforts are halted. PD-AB-SAAP may be a useful adjunctive intervention after initial SAAP therapy with a blood substitute perfusate.

EXAMPLE 4

Serial SAAP-Perflubron/Blood: Continuous SAAP versus Pulsed Diastolic SAAP

This study sought to combine all of the hypothesized beneficial elements of SAAP (aortic arch epinephrine, SAAP with perflubron, and SAAP with autologous blood as needed) and evaluate the effect on ROSC and CPP compared with a control group receiving aortic arch epinephrine. Two experimental groups were used in order to evaluate continuous SAAP infusion with CPR halted versus pulsed diastolic SAAP infusion during continued CPR.

There were three intervention groups. Animals in the control group (n=5) received standard therapy with the exception that all epinephrine doses of 0.01 mg/kg given at 3 min intervals via the aortic arch beginning at 12 min of arrest. Animals in the first experimental group (n=5) received standard therapy and aortic arch epinephrine as in the control group. In addition, they received two SAAP infusions with 300 mL of oxygenated 60% w/v perflubron emulsion beginning at 12 min and 15 min of arrest. If ROSC was not attained, autologous blood was withdrawn and reinfused at 1 min intervals beginning at 18 min of arrest. CPR was halted during SAAP and all SAAP infusions were 50 mL bolus followed by continuous infusion [SAAP-C]. Animals in the second experimental group (n=5) received the interventions with the exception that all SAAP infusions were performed as pulsed infusions during CPR-diastole [SAAP-PD].

Figure 7:
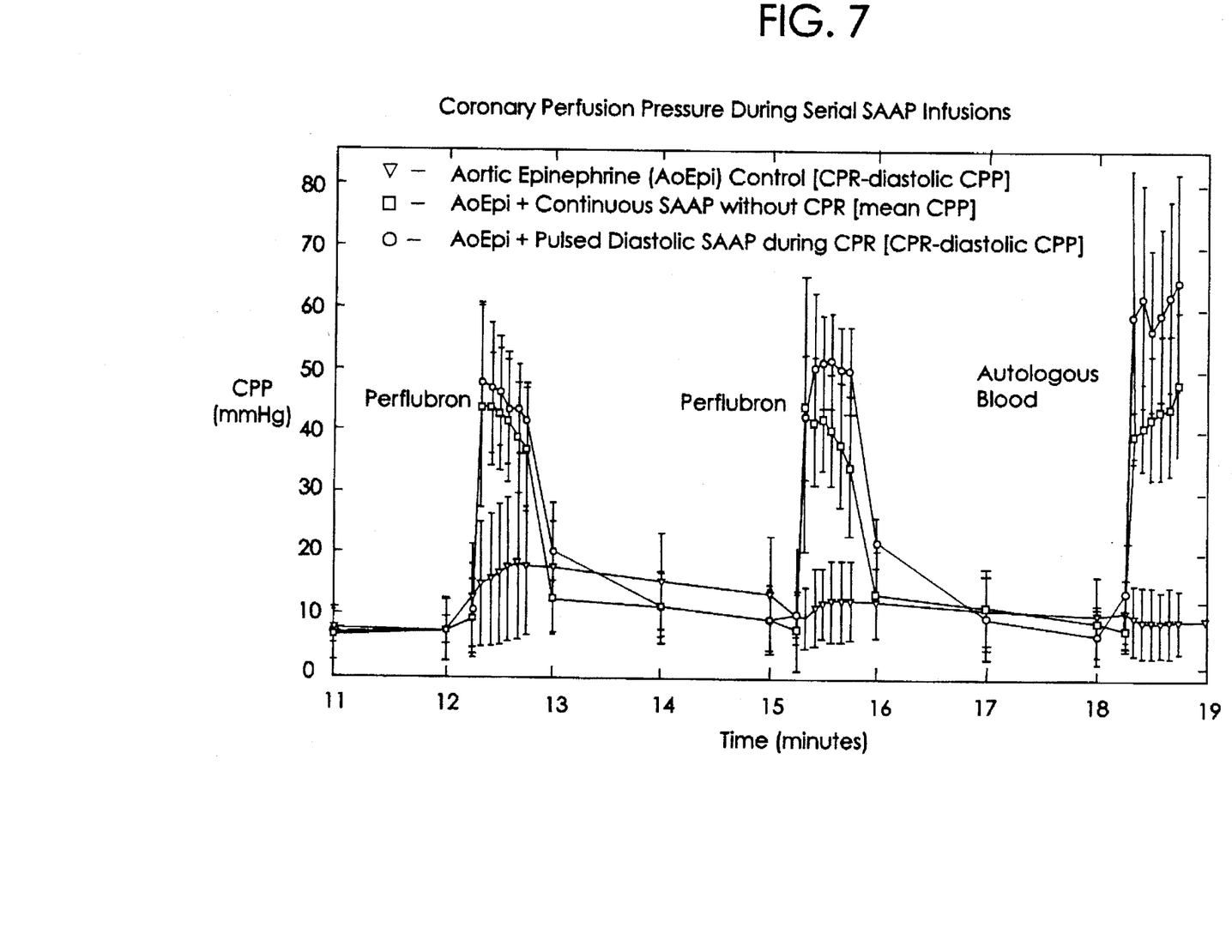
FIG. 7 is a graph plotting coronary perfusion pressure as a function of time for a control group of animals that received only epinephrine, an experimental group that received both epinephrine and continuous SAAP, and an experimental group that received epinephrine and pulsed diastolic SAAP.

ROSC and CPP data obtained by these procedures are shown in Tables 3 and 4 and in FIG. 7.

infusion periods was also much greater in both the SAAP-C group and the SAAP-PD group compared with the control group.

Fluoroscopy during the first SAAP infusion (SAAP#1) showed better perfusion of the coronary arteries with the SAAP infusate in the SAAP-C group than in the SAAP-PD group [perflubron is radiopaque due to the bromide it contains]. This suggests that stopping CPR during SAAP infusion may allow for a greater proportion of the SAAP perfusate to be directed to the myocardium.

CPP tended to be greater with SAAP-PD than SAAP-C in the second and third SAAP infusions (SAAP#2 and SAAP#3) which may be predominantly or at least partially related to achieving an adequate (or optimal) peripheral arterial vasoconstrictor response. Restoring peripheral arterial resistance has clearly been shown to improve the blood flow generated by closed-chest CPR. In the setting of SAAP-PD, an adequate vasoconstrictor response may increase the volume per minute of perfusion generated by the CPR sufficiently to result in a higher CPP (and overall greater liter/min perfusion) when combined with SAAP-PD than would be seen with SAAP-C alone without CPR.

Right atrial pressure (RAP) increases during the first two SAAP infusions (SAAP#1 and SAAP#2, perflubron) were similar for the SAAP-C and SAAP-PD groups. These RAP increases (a result of the intravascular volume loading during SAAP) were responsible for the progressive decreases in CPP which occurred during the SAAP#1 and SAAP#2 infusion periods. RAP increases during the third SAAP infusion (SAAP#3, autologous blood) were also similar for the SAAP-C and SAAP-PD groups. However, the magnitude of the RAP increases was less during SAAP#3 compared with SAAP#1 and SAAP#2. This was anticipated due to the venous blood withdrawal occurring both prior to and during the SAAP#3 infusion. The femoral venous blood withdrawal reduced the RAP prior to SAAP#3 and limited the RAP increase during SAAP#3.

The foregoing examples are illustrative of the present invention, and are not to be construed as limiting thereof. The invention is defined by the following claims, with equivalents of the claims to be included therein.

TABLE 3

| | | CPR-diastolic CPP (mmHg, mean ± S.D.) | | | | | |
|---|---|---|---|---|---|---|---|
| Group | ROSC | 12 min | SAAP#1 | 15 min | SAAP#2 | 18 min | SAAP#3 |
| Control | 1/5 | 7.0 ± 2.4 | 17.0 ± 11.6 | 12.4 ± 9.4 | 11.2 ± 6.4 | 8.5 ± 6.4 | 7.2 ± 5.2 |
| SAAP-C | 5/5* | 7.4 ± 4.8 | 41.2 ± 10.0# | 8.6 ± 5.3 | 39.4 ± 9.2# | 7.5 ± 2.6 | 42.2 ± 11.6# |
| SAAP-PD | 5/5* | 7.2 ± 4.8 | 43.2 ± 9.3# | 8.4 ± 4.8 | 50.8 ± 4.3 | 5.4 ± 4.3 | 58.0 ± 14.1# |

*<0.05 vs Control, Fisher's Exact
p < 0.05 vs Control, ANOVA

TABLE 4

| Group | ROSC | Time from Initiation of CPR to ROSC with a Systolic Aortic Pressure > mmHg for 1 minute |
|---|---|---|
| SAAP-C | 5/5 | 11.9 ± 3.9 mins |
| SAAP-PD | 5/5 | 11.4 ± 4.0 mins p = NS, SAAP-PD vs SAAP-C |

These results indicate that both SAAP-C and SAAP-PD interventions can result in significantly higher rates of ROSC than the control group receiving aortic arch epinephrine. Coronary perfusion pressure (CPP) during the SAAP That which is claimed is:

1. An apparatus for treating a subject in cardiac arrest, comprising:
   storage means for storing a protective solution;
   delivery means for delivering the protective solution to the aorta of said subject, said delivery means being fluidly connected with said storage means; and
   pulsing means connected with said delivery means for inducing the protective solution to be delivered to the aorta in a pulsatile rhythm; and
   means for repeatedly and alternatively compressing, then decompressing, the chest of said subject.
2. The apparatus of claim 1, further comprising control means for controlling the operation of said pulsing means and said compressing means such that said delivery means delivers said protective solution to said subject during decompression of the chest of said subject but fails to deliver said protective solution to said subject during compressions of the chest of said subject.

3. A method of treating a subject in cardiac arrest, comprising the steps of:

blocking the descending aorta of said subject;

perfusing the aortic arch of said subject with a protective solution in an amount effective to deliver oxygen to the heart of said subject, said perfusing step being performed so that said protective solution infuses said aorta in a pulsatile rhythm.

4. The method of claim 3, further comprising the step of administering a vasoconstrictor in an amount effective to enhance coronary perfusion with said protective solution.

5. The method of claim 3, wherein said perfusing step comprises infusing said aorta with said protective solution such that pressure variations created in said aorta thereby substantially mimic pressure variations in said aorta during normal cardiac function.

6. The method of claim 3, wherein said perfusing step is performed with sufficient pressure to flush blood cells from microvasculature of said subject.

7. The method of claim 3, wherein said perfusing step comprises infusing said aorta with said protective solution in a pulsatile rhythm such that the pressure differential experienced by said aorta is between about 5 and 75 millimeters mercury.

8. The method of claim 3, wherein the rate of the pulsatile rhythm is selected to be generally similar to the normal heart rate of said subject.

9. The method of claim 8, wherein said pulsatile rhythm rate is between about 30 and 200 cycles per minute.

10. The method of claim 3, further comprising the step of restoring spontaneous circulation to said subject.

11. The method of claim 3, wherein said blocking step comprises blocking said descending aorta of said subject with a balloon catheter, and wherein said perfusing step comprises perfusing said aortic arch with oxygenated solution through a lumen of said balloon catheter.

12. A method of treating a subject in cardiac arrest, comprising the steps of:

blocking the descending aorta of said subject;

repeatedly and alternatively compressing, then decompressing, the chest of said subject;

perfusing the aortic arch of said subject with a protective solution in an amount effective to deliver oxygen to the heart of said subject, said perfusing step being performed so that said protective solution infuses said aorta in a pulsatile rhythm during said decompressing steps.

13. The method of claim 12, wherein said perfusing step is performed so that the aortic valve of said subject is maintained in a substantially closed position.

* * * * *